(12) United States Patent
Yoon et al.

(10) Patent No.: US 7,015,337 B2
(45) Date of Patent: Mar. 21, 2006

(54) PROCESS FOR PREPARING 5-AMINOMETHYL-2-THIOPHENECARBONITRILE HCL BY ONE-POT REACTION

(75) Inventors: Suk Kyoon Yoon, Taejeon (KR); Bong Chan Kim, Taejeon (KR); Won Hyuk Jung, Taejeon (KR); Jae Chul Lee, Taejeon (KR); Koo Lee, Taejeon (KR); Cheol Won Park, Taejeon (KR)

(73) Assignee: LG Life Sciences Ltd., Seoul (KR)

( * ) Notice: Subject to any disclaimer, the term of this patent is extended or adjusted under 35 U.S.C. 154(b) by 300 days.

(21) Appl. No.: 10/473,887

(22) PCT Filed: Mar. 15, 2002

(86) PCT No.: PCT/KR02/00450

§ 371 (c)(1),
(2), (4) Date: Oct. 2, 2003

(87) PCT Pub. No.: WO02/081465

PCT Pub. Date: Oct. 17, 2002

(65) Prior Publication Data

US 2004/0116714 A1     Jun. 17, 2004

(30) Foreign Application Priority Data

Apr. 4, 2001   (KR) ............................... 2001-17840

(51) Int. Cl.
*C07D 333/38* (2006.01)
(52) U.S. Cl. ...................................................... 549/61
(58) Field of Classification Search .................. 549/61
See application file for complete search history.

(56) References Cited

U.S. PATENT DOCUMENTS

| 5,707,966 A | 1/1998 | Schacht et al. |
| 5,914,319 A | 6/1999 | Schacht et al. |
| 6,392,048 B1 * | 5/2002 | Sasaki et al. ............... 546/287 |
| 6,541,632 B1 * | 4/2003 | Ogino et al. ................ 544/336 |

FOREIGN PATENT DOCUMENTS

WO   WO 2000/39124 A   7/2000

* cited by examiner

*Primary Examiner*—Deborah C. Lambkin
(74) *Attorney, Agent, or Firm*—Birch, Stewart, Kolasch & Birch, LLP

(57) ABSTRACT

The present invention provides a novel process for preparing a compound represented by the above formula 7, which is an important intermediate for an oral thrombin inhibitor, by one-pot reaction. In accordance with the present invention, the above intermediate for the thrombin inhibitor may be obtained in a high yield.

8 Claims, No Drawings

PROCESS FOR PREPARING 5-AMINOMETHYL-2-THIOPHENECARBONITRILE HCL BY ONE-POT REACTION

This application is the national phase under 35 U.S.C. § 371 of PCT International Application No. PCT/KR02/00450 which has an International filing date of Mar. 15, 2002, which designated the United States of America.

TECHNICAL FIELD

The present invention relates to a new process for preparing 5-aminomethyl-2-thiophenecarbonitrile.HCl of formula 7 below, and specifically, to a process for preparing 5-aminomethyl-2-thiophenecarbonitrile.HCl of formula 7 by one-pot reaction.

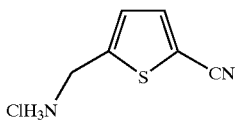

7

BACKGROUND ART

The compound of formula 7 is not only an important moiety forming N-terminal group of a pharmaceutical raw material (ref. Korean Patent Application Nos. 1998-0060266 and 1999-0033490; WO 00/39124) developed as a novel thrombin inhibitor for oral administration, but also one moiety of a compound (ref. International Application No. PCT/US95/02558; WO 95/23609) developed and effectively used for prohibition of blood coagulation and treatment of thrombosis of a mammal. Therefore, more attention is gradually drawn to preparing the compound of formula 7 above.

DISCLOSURE OF THE INVENTION

In this circumstance, the present inventors have studied extensively a preparation process of the above compound of formula 7, and then, found a novel process for preparing the above compound of formula 7 by one-pot reaction. Through such a new scheme and process, the compound of formula 7 could be obtained in a high yield and a low cost. Thus, the present invention has been completed.

Therefore, the object of the present invention is to provide a new process for preparing the compound of formula 7 below which comprises the steps of:
a) reacting the compound of formula 1 with hydroxylamine to produce a compound of formula 2,
b) O-acetylating the obtained compound of formula 2 to produce a compound of formula 3,
c) removing an acetyl group of the obtained compound of formula 3 and introducing a cyano group therein to produce a compound of formula 4,
d) brominating a moiety of methyl group in the obtained compound of formula 4 to produce a compound of formula 5,
e) subjecting the obtained compound of formula 5 to an azide reaction to produce a compound of formula 6, and
f) subjecting the obtained compound of formula 6 to a reaction for producing iminophosphorane and then hydrolysing the resultant.

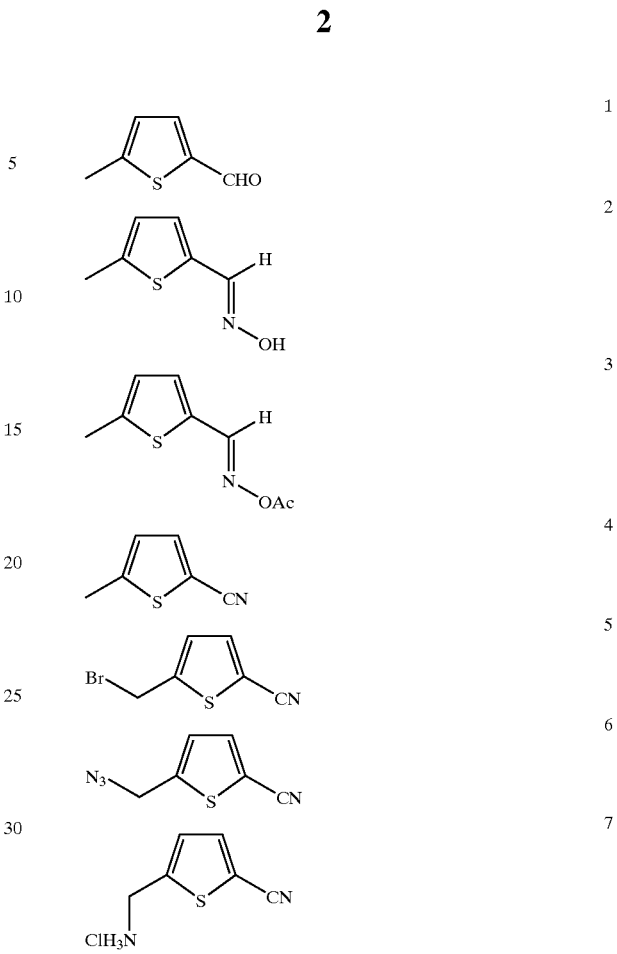

wherein, Ac is an acetyl group.

BEST MODE FOR CARRYING OUT THE INVENTION

The present invention is decribed in more detail below.

The present invention provides a process for preparing the compound of formula 7 from the compound of formula 1 through the above reaction procedures.

Since the preparation process in accordance with the present invention may be carried out by one-pot reaction, particularly in a single reaction solvent, there is no need for a solvent distillation procedure and for distillation procedures in obtaining reaction intermediates. In addition, the present process has many advantages, such as easy mass production, cost reduction, yield increase, etc.

The term "single reaction solvent" used in the present invention includes benzene, carbon tetrachloride, cyclohexane, dichloromethane, chloroform, dichloroethane, tetrachloroethane, hexachloroethane, hexane, xylene and the like.

Abbreviations used through the specification of the present invention are explained as follows:

| | |
|---|---|
| Ac: | acetyl group |
| NBS: | N-bromosuccinimide |
| AIBN: | 2,2'-azobis(2-methylpropionitrile) |
| TBABr, TBAB: | tetrabutylammonium bromide |
| Ph: | phenyl |

-continued

| | |
|---|---|
| Et: | ethyl |
| TFA: | trifluoroacetic acid |
| Me: | methyl |
| min: | minute |
| EA: | ethylacetate |
| DAMT-CN: | diazidomethylthiophenecarbonitrile |
| DBMT-CN: | dibromomethylthiophenecarbonitrile |
| MDC: | methylene chloride |
| Boc: | tert-butoxycarbonyl |
| THF: | tetrahydrofuran |

An embodiment of the process of the present invention is illustrated in the following reaction scheme 1:

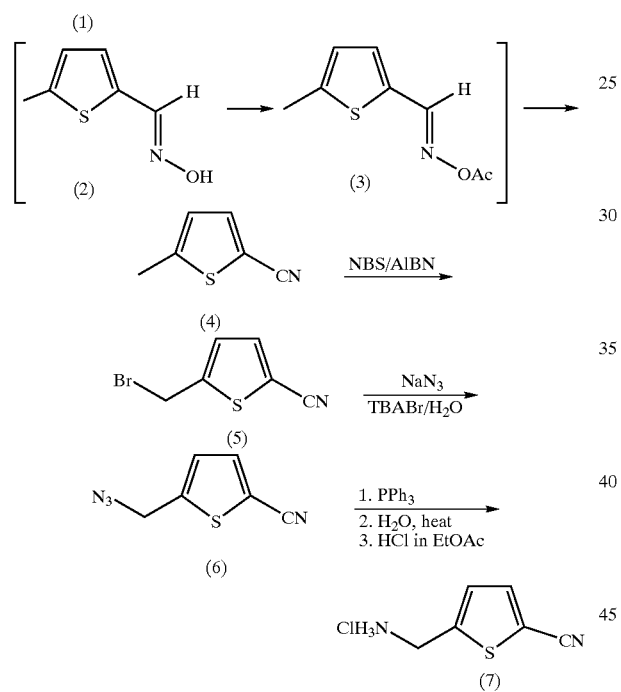

Hereinafter, the above reaction is explained in detail with reaction conditions including amounts of reagents, reaction temperatures, separation methods and the like In the first reaction, 1.1 equivalents of hydroxylamine hydrochloride salt and 1.1 equivalents of pyridine are added to the compound (1) of the starting material and the obtained mixture is stirred. When pyridine is added thereto, the reaction is high exothermic, and so pyridine is slowly added with sufficient cooling. After stirring the mixture for 10 minutes, a reaction solvent is added thereto and heated. The obtained water may be removed by using Dean-Strark apparatus to obtain the oxime compound (2).

After confirming exhaustion of the starting compound (1) by. PLC, 1.1 equivalents of pyridine are further added thereto. Then, acetic anhydride is added to the mixture to be acetylated. When the reactant is heated, the desired compound (3) may be obtained. At this time, if the reaction is proceeded without acetylation, the reaction is slowly carried out. The remaining hydroxyl amine and the obtained compound (3) are reacted to produce amidoxime compound (See: Synthesis, 1982, 190). A method to promote the reaction by using anhydrous formic acid is known to prevent this phenomenon (See: Synthesis, 1978, 112). However, there are disadvantages that anhydrous formic acid is hard to produce and expensive. These disadvantages may be solved with a reaction using acetic anhydride or trifluoroacetic anhydride.

Thereafter, by slowly heating the reaction solution, a compound (4) is obtained by removing an acetyl group from the compound (3) and introducing a cyanide group.

The process for preparing the compound of formula 7 from the compound of formula 4, that is, the process for preparing the compound of formula 7 with a hydrochloride salt by converting a moiety of methyl group to an aminomethyl group is set forth in Korean Patent Application Nos. 1998-0060266 and 1999-0033490 cited above as follows:

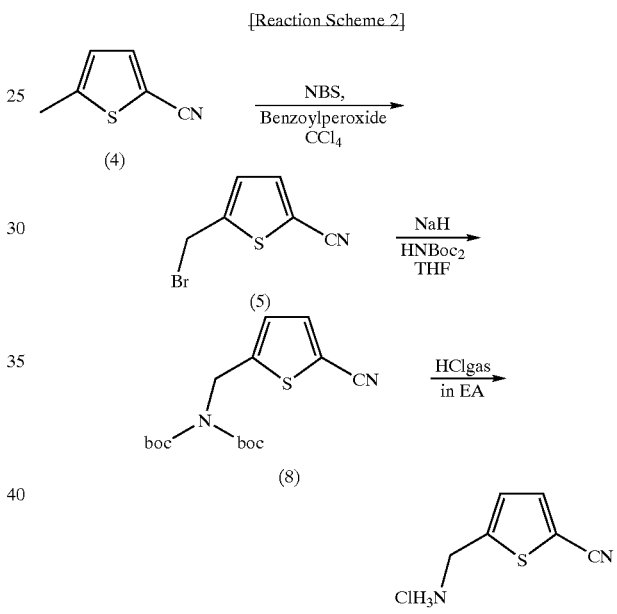

But, there is a disadvantage that iminodicarboxylic acid di-t-butyl ester [(Me₃COCO)₂NH] is very expensive, which could be a problem in case of mass production in developing goods in the future.

Accordingly, the present inventors found that the compound of formula 7 could be obtained through the following procedures, so as to continuously carry out the present process, particularly in a single reaction solvent.

The compound of formula 4 is brominated to produce a compound of formula 5, which is subjected to an azide reaction to produce a compound of formula 6. The obtained compound of formula 6 is hydrolized after going through a reaction for producing iminophosphorane.

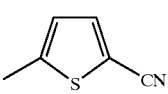

4

-continued

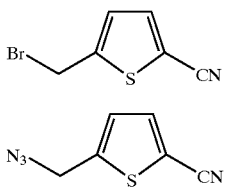

In the above process, an azidating agent is selected from the group consisting of $NaN_3$ and $KN_3$. Furthermore, preferably, the azide reaction is carried out in the presence of a phase transfer catalyst. The phase transfer catalyst is also selected from the group consisting of benzyltriethylammonium chloride, tetrabutylammonium bromide, methyltrioctylammonium chloride, and hexadecyltrimethylammonium chloride.

As shown in the above reaction scheme 1, this process may be illustrated as follows:

The compound (4) is dissolved in cyclohexane, benzene, carbon tetrachloride, dichloromethane, chloroform, dichloroethane, tetrachloroethane, hexachloroethane, hexane, or xylene, and then heated. 0.9 equivalents of NBS and 0.01 equivalents of AIBN [2,2'-azobis(2-methylpropionitrile)] are mixed and added to the solution in a small quantity. NBS is used in an amount of 0.9 equivalents, and AIBN in an amount of 0.01 equivalents. The reaction temperatures vary from 60° C. to 85° C. depending on solubilizing solvents. Therefore, a bromo compound (5) is obtained.

Sodium azide ($NaN_3$) may be dropwise added to the bromo compound (5) at room temperature in presence of a phase transfer catalyst to obtain an azido compound (6). As the phase transfer catalyst, quaternary ammonium compounds, such as benzyltriethylammonium chloride, tetrabutylammonium bromide, methyltrioctylammonium chloride, hexadecyltrimethylammonium chloride and the like, are used. Since these quaternary ammonium compounds have large organic groups, they have solubility in both water and organic solvents. In case of reacting $NaN_3$, $Na^+N_3^-$ is dissolved in an aqueous layer, but not in an organic layer. Therefore, $NaN_3$ is reacted with a quaternary ammonium compound to transfer to the organic layer, in which the reaction is occurred. For example, in case of using tetrabutylammonium bromide, $Na^+N_3^-$ in the aqueous layer forms $Bu_4NN_3$ to transfer to the organic layer, and then $N_3^-$ is reacted.

1.0 Equivalent of triphenylphospine ($PPh_3$) is subdivided at a temperature less than 30° C. and added to the compound (6), and the mixture is stirred at room temperature. After stirring the mixture, water is added thereto and heated at 50° C. The amount of triphenylphospine may be 1.0 to 1.5 equivalents, and the heating temperature may be varied from 50° C. to 150° C. depending on a solubilizing solvent. Such an obtained compound may be treated with acid-base, and then with hydrochloric inorganic solution to obtain the compound (7) as solid.

As shown above, the preparation process of the present invention can obtain the final material most effectively by a continuous reaction in a single reaction solvent. In addition, in case of preparing the compound of formula 7 in accordance with the process of the present invention, the following advantages can be confirmed:

1) By using only one reaction solvent, there is no need for any distillation procedure of solvent, compared to previous methods, 2) When reaction intermediates are obtained, there is no need for any distillation and purification procedures, 3) Dibromo compound (dibromomethylthiophene carbonitrile, DBMT-CN) produced under reaction may be removed by filtration without distillation after the final reaction, 4) An azido compound (compound of formula 6) having danger of explosion is used in the next reaction as it is, without distillation process, 5) Providing a method to remove all the previous impurities by filtering the compound of formula 7 as crystals, 6) The un-reacted compound (4) occuring after bromination may be recovered from filtrate in the final step and used again, and 7) Finally, since the reaction is symplified by using a single reaction solvent, mass production is easily achieved. Furthermore, there are such advantages as cost reduction, shortened cycle time, suppression of waste solvent, and overall yield increase, etc.

The present invention is explained in detail by way of the following examples, which are not intended to limit the technical scope of the present invention.

EXAMPLE 1

Preparation of 2-{[(acetyloxy)imino]methyl}-5-methylthiophene (3)

1.20 kg (9.51 moles) of 5-methyl-2-thiophenecarboxaldehyde and 727 g (10.46 moles) of $NH_2OH.HCl$ were placed in a reaction vessel and cooled to 10° C. Then, 0.85 L (10.46 moles) of pyridine was dropwise added thereto for 1 hour (an exothermic reaction: 10° C.→43° C). After 10 minutes, 7 L of benzene was added thereto and heated to remove the obtained water by Dean-Stark apparatus (initial internal temperature: 80° C.). After 165 mL of water was collected for 8 hours, (theoretical quantity: 171 mL), the product was cooled to obtain 5-methyl-2-thiophenecarboxaldehyde oxime. At this time, if stirring was stopped, two-phases were formed. After 0.85 L (10.46 moles) of pyridine was completely added at 15° C., 1.26 kg (12.36 moles) of $Ac_2O$ was dropwise added thereto for 25 minutes, with maintaining a temperature less than 15° C. The reaction mixture was stirred for 1 hour at room temperature, and completion of the acetylation reaction was confirmed by HPLC (2 phases).

[HPLC]: 260 nm, 1.0 ml/min., Capcell pak $C_{18}$

|  | Compound | | | |
| --- | --- | --- | --- | --- |
|  | Pyridine | Oxime | Oxime | Compound (4) |
| (Oxime) RT | 2.65 | 12.22 | 12.94 | 21.96 |
| Area % | 22.14 | 45.27 | 16.47 | 15.74 |

|  | Compound | | | |
| --- | --- | --- | --- | --- |
|  | Pyridine | Compound (3) | Compound (4) | Compound (3) |
| (Compound (3)) RT | 2.62 | 20.22 | 22.05 | 22.54 |
| Area % | 45.15 | 33.81 | 5.01 | 15.21 |

[Gradient conditions] initial: 75/25 ($H_2O$/MeCN, 0.1% TFA), 15 min.: 75/25, 25 min.: 65/35, 27 min.: 75/25

EXAMPLE 2

Preparation of 5-methyl-2-thiophenecarbonitrile (4)

After confirming completion of the acetylation reaction, the reaction solution was slowly heated and the obtained clear solution was stirred at 70° C. for 1.5 hours. After confirming completion of the reaction by HPLC, the solution was cooled to room temperature. The obtained organic layer was washed with 5 L of $H_2O$, 2 L of 1N HCl (2 times), 2 L of $H_2O$, and finally 1 L of 5% NaCl+1 L of 5% $NaHCO_3$. The organic layer was dried by adding anhydrous $Na_2SO_4$, filtered, and washed with 1 L of benzene. Then, the organic layer was again placed in the reaction vessel (total volume: 6.3 L).

[HPLC]: 260 nm, 1.0 ml/min., Capcell pak $C_{18}$

|  | Compound | |
|---|---|---|
|  | Pyridine | Compound (4) |
| RT | 2.66 | 22.06 |
| Area % | 45.25 | 53.34 |

[Gradient conditions] initial: 75/25 ($H_2O$/MeCN, 0.1% TFA), 15 min.: 75/25, 25 min.: 65/35, 27 min.: 75/25

EXAMPLE 3

Preparation of 5-(bromomethyl)-2-thiophencarbonitrile (5)

1.69 kg (9.51 moles) of NBS and 156 g (0.95 moles) of AIBN were well mixed and placed in a vinyl wrapper (at this time, the previous reaction was regarded to be proceeded to 100%). The benzene solution of Example 2 was heated. The NBS-AIBN mixture was portionwise added to the heated solution at 73° C. for 40 minutes. The solution was refluxed for 1.5 hours after the addition was done. After confirming completion of the reaction by HPLC, the solution was cooled to room temperature. The reaction solution was washed with [1 L of $H_2O$+4 L of 5% $NaHCO_3$], and then [2 L of $H_2O$+1 L of 5% NaCl].

[HPLC]: 260 nm, 1.0 ml/min., Capcell pak $C_{18}$

|  | Compound | | | |
|---|---|---|---|---|
|  | Compound (4) | Compound (5) | Benzene | DBMT-CN |
| RT | 2.65 | 12.22 | 12.94 | 21.96 |
| Area % | 22.14 | 45.27 | 16.47 | 15.74 |

[Isocratic conditions] $H_2O$ (0.1% TFA):MeCN(0.1% TFA)=55:45

EXAMPLE 4

Preparation of 5-(azidomethyl)-2-thiophenecarbonitrile (6)

At room temperature, 1.0 L of $H_2O$ and 46 g (0.143 moles/1.7%) of TBAB (tetrabutylammonium bromide were added to the solution of the compound (5) in benzene (7.13 moles; it was assumed that 75% of 5-(bromomethyl)-2-thiophenecarbonitrile (5) was obtained from 5-methyl-2-thiophenecarbonitrile (4); this assumption was based on the previous data of HPLC) were added), prepared in Example 3. 557 g (8.56 moles, 1.2 eq.) of $NaN_3$ was added thereto at room temperature. Then, the solution was stirred for 1 hour to complete the reaction. Completion of the reaction was confirmed by HPLC. After taking out $H_2O$, the organic layer was washed again with 2 L of $H_2O$.

[HPLC]: 260 nm, 1.0 ml/min., Capcell pak $C_{18}$

|  | Compound | | | | |
|---|---|---|---|---|---|
|  | Compound(4) | Compound(6) | Benzene | DAMT-CN | DBMT-CN |
| RT | 7.56 | 7.96 | 9.74 | 12.66 | 14.58 |
| Area % | 12.85 | 71.62 | 5.24 | 0.63 | 6.89 |

[Isocratic conditions] $H_2O$ (0.1% TFA):MeCN(0.1% TFA)=55:45

EXAMPLE 5

Preparation of 5-(aminomethyl)-2-thiophenecarbonitrile.HCl (7)

(Reaction for Producing Iminophosphorane)

The solution of the azido compound (6) of Example 3 in benzene (7.13 moles; it was assumed that 75% of the compound (5) was obtained from the compound (4); this assumption was based on the HPLC data) was cooled to 15° C. Then, 1.95 kg (7.41 moles) of $PPh_3$ was added to the solution, over 5 times in portion over 2 hours. After stirring the solution at room temperature for 1.5 hours, completion of the reaction was confirmed by HPLC. Then, the solution was heated to 70° C., with adding 1.28 L (71.3 moles) of $H_2O$ thereto.

[HPLC]: 260 nm, 1.0 ml/min., Capcell pak $C_{18}$

|  | Compound | | | |
|---|---|---|---|---|
|  | Compound (7) | Iminophosphorane | Compound (4) | $PPh_3$=O |
| RT | 2.53 | 6.02 | 7.54 | 8.16 |
| Area % | 18.27 | 57.89 | 13.40 | 4.16 |

[Isocratic conditions] $H_2O$ (0.1% TFA):MeCN(0.1% TFA)=55:45

(Reaction for Producing $NH_2$: Hydrolysis of Iminophosphorane).

After stirring the reaction solution at 70° C. for 3 hours, completion of the reaction was confirmed by HPLC and the solution was cooled to room temperature.

[HPLC]: 260 nm, 1.0 ml/min., Capcell pak $C_{18}$

|  | Compound | | | | | |
|---|---|---|---|---|---|---|
|  | Compound (7) | Compound (4) | $PPh_3$=O | Benzene | DAMT-CN | DBMT-CN |
| RT | 2.53 | 7.52 | 8.12 | 9.68 | 11.17 | 14.49 |
| Area % | 59.5 | 14.1 | 11.28 | 4.92 | 0.89 | 3.38 |

[Isocratic conditions] H$_2$O (0.1% TFA):MeCN(0.1% TFA)=55:45

(Work-Up and Production of HCl Salt)

The reaction solution was extracted twice with 3 L of 2N HCl. The combined aqueous layer was washed with 3 L of MDC (methylene chloride). The aqueous layer was cooled to 10° C. and it pH was adjusted to about 10 by adding 460 g of NaOH under 20° C. The aqueous layer was extracted with 5 L of MDC, and then again with 2 L of MDC. The combined MDC layer was placed in the reaction vessel (total volume: 8.1 L) and concentrated under reduced pressure. 7 L of Et$_2$O was introduced into the residue, and 2.12 L of a solution of about 3N HCl in EtOAc was dropwise added thereto under 25° C. After stirring the reaction mixture at room temperature for 1 hour, the resulting solid was filtered, and then, the filtered solids were washed with 3 L of Et$_2$O and 2 L of EtOAc and dried under nitrogen flow. Dry weight: 1.09 kg (total yield: 65.8%)

[HPLC]: 260 nm, 1.0 ml/min., Capcell pak C$_{18}$

| | Compound | | |
|---|---|---|---|
| | Compound (7) | Compound (4) | DBMT-CN |
| RT | 6.55 | 12.43 | 14.28 |
| Area % | 95.48 | 1.06 | 0.33 |

[Gradient conditions] initial: 94/6 (H$_2$O/MeCN, 0.1% TFA), 6 min.: 94/6, 16 min.: 55/45, 26 min.: 55/45, 30 min.: 94/6

$^1$H NMR (CD$_3$OD) δ 7.77 (d, 1H), 7.34 (d, 1H), 4.41 (s, 2H) FAB MS: 139 [M+1]$^+$

INDUSTRIAL AVAILABILITY

In accordance with the present process, intermediates for preparing a thrombin inhibitor may be synthesized in a high yield by continuous reaction using a single reaction solvent from the above compound of formula 1. Therefore, the present process is suitable for mass production.

The invention claimed is:

1. A process for preparing a compound of formula 7 which comprises the steps of:
   a) reacting a compound of formula 1 with hydroxylamine to produce a compound of formula 2,
   b) O-acetylating the obtained compound of formula 2 to produce prepare a compound of formula 3,
   c) removing an acetyl group of the compound of formula 3 and introducing a cyano group therein to prepare a compound of formula 4,
   d) brominating a moiety of methyl group in the obtained compound of formula 4 to prepare a compound of formula 5,
   e) subjecting the obtained compound of formula 5 to an azide reaction to prepare a compound of formula 6, and
   f) subjecting the obtained compound of formula 6 to a reaction for producing iminophosphorane and then hydrolysing the obtained reactant

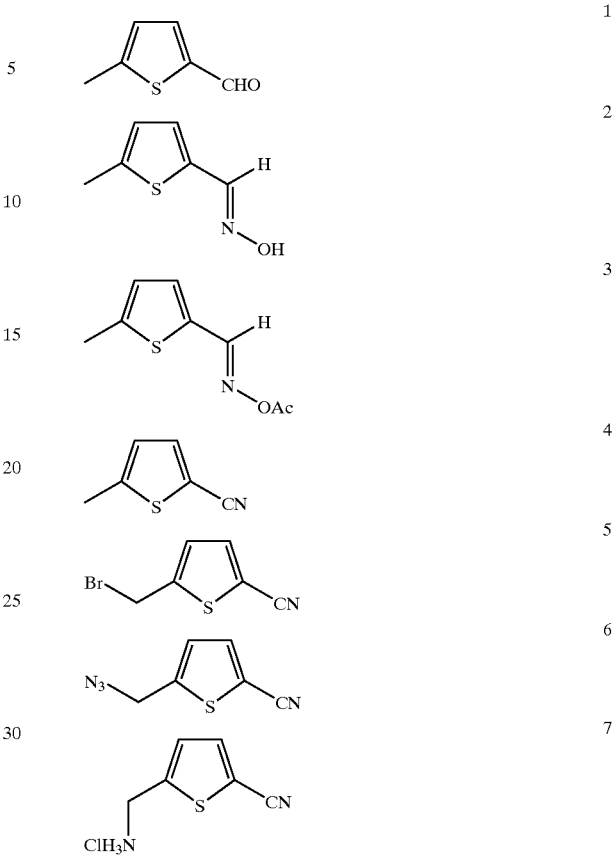

wherein, Ac is an acetyl group.

2. The process of claim 1, wherein the steps a), b), c), d), e) and f) are carried out by one-pot reaction.

3. The process of claim 1, wherein the steps a), b), c), d), e) and f) are carried out in a single reaction solvent.

4. The process of claim 3, wherein the single reaction solvent is selected from the group consisting of benzene, carbon tetrachloride, cyclohexane, dichloromethane, chloroform, dichloroethane, tetrachloroethanethane, hexane and xylene.

5. The process of any one of claims 1 to 4, wherein acetic anhydride or trifluoroacetic anhydride is used in the step b) as an acetylating agent.

6. The process of any one of claims 1 to 4, wherein a phase transfer catalyst is used in the step e).

7. The process of claim 6, wherein the phase transfer catalyst is selected from the group consisting of benzyltriethylammonium chloride, tetrabutylammonium bromide, methyltrioctylammonium chloride and hexadecyltrimethylammonium chloride.

8. The process of any one of claims 1 to 4, wherein an azide agent of the step e) is selected from the group consisting of NaN$_3$ and KH$_3$.

* * * * *